US005769832A

United States Patent [19]
Hasse

[11] Patent Number: 5,769,832
[45] Date of Patent: *Jun. 23, 1998

[54] ABSORBENT ARTICLE WITH ODOR MASKING AGENTS RELEASED BY THE FASTENING SYSTEM

[76] Inventor: Margaret Henderson Hasse, The Procter & Gamble Company, Winton Hill Technical Center 6100 Center Hill Ave., Cincinnati, Ohio 45224

[ * ] Notice: This patent issued on a continued prosecution application filed under 37 CFR 1.53(d), and is subject to the twenty year patent term provisions of 35 U.S.C. 154(a)(2).

[21] Appl. No.: 635,221

[22] Filed: Apr. 17, 1996

[51] Int. Cl.$^6$ ........................................... A61F 13/15
[52] U.S. Cl. .......................... 604/359; 604/389; 604/391
[58] Field of Search ................... 604/359–361, 604/389–391

[56] References Cited

U.S. PATENT DOCUMENTS

| | | | |
|---|---|---|---|
| 1,646,880 | 3/1927 | Schaffer | 604/359 |
| 3,977,992 | 8/1976 | Hofacker | 252/316 |
| 3,996,156 | 12/1976 | Matsukawa et al. | 252/316 |
| 4,002,458 | 1/1977 | Hofacker | 71/27 |
| 4,186,743 | 2/1980 | Steiger | 128/284 |
| 4,317,449 | 3/1982 | Nowakoski | 604/390 |
| 4,409,156 | 10/1983 | Hoshi et al. | 264/4.33 |
| 4,460,364 | 7/1984 | Chen et al. | 604/387 |
| 4,487,801 | 12/1984 | Trunbull et al. | 428/313.5 |
| 4,493,869 | 1/1985 | Sweeny et al. | 428/201 |
| 4,528,226 | 7/1985 | Sweeny | 428/40 |
| 4,606,956 | 8/1986 | Charbonneau et al. | 428/40 |
| 4,654,256 | 3/1987 | Doree et al. | 428/304.4 |
| 4,661,388 | 4/1987 | Charbonneau | 428/43 |
| 4,720,417 | 1/1988 | Sweeny et al. | 428/201 |
| 4,720,423 | 1/1988 | Fraser | 428/313.5 |
| 4,769,264 | 9/1988 | Dreger | 428/40 |
| 4,774,133 | 9/1988 | Doree et al. | 428/321.5 |
| 4,847,124 | 7/1989 | Lux née Andrieux | 428/34.2 |
| 4,874,129 | 10/1989 | DiSapio et al. | 239/36 |
| 4,889,755 | 12/1989 | Charbonneau | 428/42 |
| 4,895,567 | 1/1990 | Colon et al. | 604/389 |
| 4,961,871 | 10/1990 | Michael | 252/174.11 |
| 4,988,557 | 1/1991 | Charbonneau | 428/204 |
| 5,013,473 | 5/1991 | Norbury et al. | 252/174.13 |
| 5,126,061 | 6/1992 | Michael | 252/86 |
| 5,180,637 | 1/1993 | Sumii | 428/402.21 |
| 5,221,276 | 6/1993 | Battrell | 604/391 |
| 5,249,676 | 10/1993 | Ashcraft et al. | 206/264 |
| 5,342,333 | 8/1994 | Tanzer et al. | 604/359 |
| 5,342,420 | 8/1994 | Bosses | 55/279 |
| 5,364,380 | 11/1994 | Tanzer et al. | 604/359 |
| 5,391,420 | 2/1995 | Bootman et al. | 428/195 |
| 5,395,047 | 3/1995 | Pendergrass, Jr. | 239/56 |
| 5,429,628 | 7/1995 | Trinh et al. | 604/359 |

Primary Examiner—Robert A. Clarke
Assistant Examiner—Ki Yong O
Attorney, Agent, or Firm—Theodore P. Cummings; Steven W. Miller; Jacobus C. Rasser

[57] ABSTRACT

The present invention relates to an absorbent article and preferably a diaper or incontinent device having perfume-filled release agents, preferably being perfume-filled microcapsules, disposed on the diaper fastening system. The encapsulated agents and/or odor masking agents are released subsequent to the removal of the article from about the wearer, i.e., as the fastening system is disconnected, the microcapsules burst, thereby releasing the agents to the air containing the malodor constituents.

16 Claims, 6 Drawing Sheets

ABSORBENT ARTICLE WITH ODOR MASKING AGENTS RELEASED BY THE FASTENING SYSTEM

FIELD OF INVENTION

The present invention relates to an absorbent article which comprises a fastening system that contains encapsulated malodor masking agents such that upon removal of the article from the wearer, the malodor masking agents are released to mask/cloak exudate odors.

BACKGROUND OF THE INVENTION

A wide variety of fluid absorbent structures known in the art absorb body fluids such as blood, urine, menses, and the like, and are sanitary and comfortable in use. Disposable products of this type generally comprise fluid-permeable topsheet material, fluid absorbent core, and fluid-impermeable backsheet material. Various shapes, sizes and thicknesses of such articles have been explored in an attempt to make their use more comfortable and convenient.

Odor control in sanitary products has been under investigation for many years. Many body fluids have an unpleasant odor, or develop such odors when in contact with air and/or bacteria for prolonged periods.

Various odor-controlling agents have been disclosed in the literature. For example, U.S. Pat. No. 4,525,410, Hagiwara et al., issued Jun. 25, 1985, teaches zeolite particles (doped with bactericidal cations) stably held in a fibrous web by incorporating some portion of meltable fibers in the web, and applying heat. Hagiwara et al. teaches using these compositions as the outside cover layer in general sanitary goods.

U.S. Pat. No. 2,690,415, F. A. Shuler, issued Sep. 28, 1954, teaches particles of odor-absorbing materials uniformly affixed at the interstices of a permeable web by adhesive to provide an odor absorbent medium, e.g., catamenials. Particulate carbon, silica gel and activated alumina are noted. Shifting and/or displacement of the particulates is avoided and the sheet is flexible.

ABSCENTS (odor-control molecular sieve from Union Carbide) for use in diapers and catamenials are specifically noted in Union Carbide brochure (A. J. Gioffre 1988). The brochure indicates that Union Carbide's market research shows potential benefits in such products. U.S. Pat. Nos. 4,795,482 and 4,826,497, relate to ABSCENTS used as an odor-controlling agent, generally, and in sanitary products, in particular.

Activated carbon is a very effective odor absorber, with average internal surface area of about 1000 $m^2/g$. However, activated carbon is not readily incorporated into consumer products.

Zeolites have smaller surface area, in the range of about 400–800 $m^2/g$. However, zeolites may absorb the moisture in body fluids (i.e., water) over other fluids, which may compromise its effectiveness. Furthermore, activated carbon and zeolites have open structures, and continuously absorb airborne organic vapor, unless hermetically sealed. Therefore, during storage, these odor adsorbents can become saturated and less efficient before the products are used.

Consumers use body malodor to determine the need for change of a diaper, catamenial and the like. Therefore, using odor masking or encapsulated agents in an absorbent article core, topsheet or backsheet would hinder a consumer's ability to properly judge article removal times. For example as a consumer's sensitivity to a masking fragrance would decrease as it is released within an article, discernment of the time to remove a diaper or catamenial would decrease also.

Consumers desire not to be exposed to body malodor, but masking these odors while the absorbent article is in use is not preferable. Thus, applicant's invention allows consumers to mask body malodor upon the removal of the article from the wearer.

SUMMARY OF THE INVENTION

Accordingly, the present invention provides a diaper that has a first waist region and a second waist region. The diaper further comprises a fluid pervious topsheet, a fluid impervious backsheet joined to the topsheet, an absorbent core located between the topsheet and the backsheet, a fastening system for securing the absorbent article on a wearer, and perfume-filled release agents disposed on the fastening system. The perfume-filled release agents are released upon disengagement of the fastening system.

Preferably, the perfume-filled release agents are microcapsules that comprise perfume selected from the group consisting of uncomplexed cyclodextrins, perfumes, zeolites, activated carbons and mixtures thereof. In a preferable embodiment, the fastening system comprises at least one pair of first fastening members disposed in the first waist region and at least one second fastening member disposed in the second waist region.

In one embodiment, the first fastening member comprises hooks, and the second fastening member comprises loops. In a preferred embodiment, the first fastening member comprises adhesive tape tabs, and the second fastening member comprises a tape tab receiving zone. In yet another embodiment, the first fastening member comprises adhesive tape tabs and hooks, and the second fastening member comprises loops and at least one tape tab receiving zone.

Microcapsules can be joined to the first fastening member of the fastening system, or to the second fastening member of the fastening system, or both. Also, microcapsules can provide a fragrance burst of perfume and/or diffusely release perfume at a steady-state at disengagement of the first and second fastening members. Alternatively, microcapsules can provide a fragrance burst and/or diffusely release perfume at a steady-state at engagement of the first and second fastening members alone or in combination with a release of perfume at disengagement of the first and second fastening members.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "diaper" refers to an absorbent article generally worn by infants and incontinent persons that is worn about the lower torso of the wearer which absorbs and contains body exudates, and, more specifically, refers to devices which are placed against or in proximity to the body of the wearer. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). The term "perfume" as used herein refers to odor absorbing and/or masking agents such as volatile perfumes, essences, fragrances, zeolites, activated carbon, cyclodextrins, mixtures thereof and the like which are placed in microcapsules that are subsequently burst by mechanical shearing forces and/or uncovered to release the perfume as a result of diffusion. The term "release agent" as used herein refers to any suitable means known in the art for the containment and release of perfume as described herein. The term "microcapsules" or "microspheres" as used herein refers to a release agent and/or containment assembly for holding and later distributing perfume. The term "perfume-filled" as used herein refers to microcapsules that are at least partially filled with perfume as defined herein. The term "fragrance burst" as used herein refers to the immediate release of perfume resulting from bursting perfume-filled microcapsules that contain perfume. The term "diffuse" or "steady-state" as used herein refers to a substantially continuous release of perfume from a perfume-filled release agent. By the term "embedded" it is meant herein the integration or securement of one material within another material, adjacent to another material, and/or onto another material, e.g., microcapsules embedded on a substrate by a securement means.

Preferably, the release agents for all embodiments disclosed herein are microcapsules which are perfume-filled. At the shearing or bursting of such a microcapsule, at least one opening will be created on the surface of the previously unopened microcapsule through which perfume will diffuse through one of the mechanisms disclosed herein (e.g., fragrance burst, steady-state diffusion etc.) Alternatively, the microcapsule can be a porous, substantially filled-in structure that releases perfume through one or more disclosed mechanisms as the microcapsule is uncovered. By the term "uncovered" it is meant herein that a structure, which had been previously substantially covered from full exposure to the air by a covering means, is now exposed.

Figure 1:
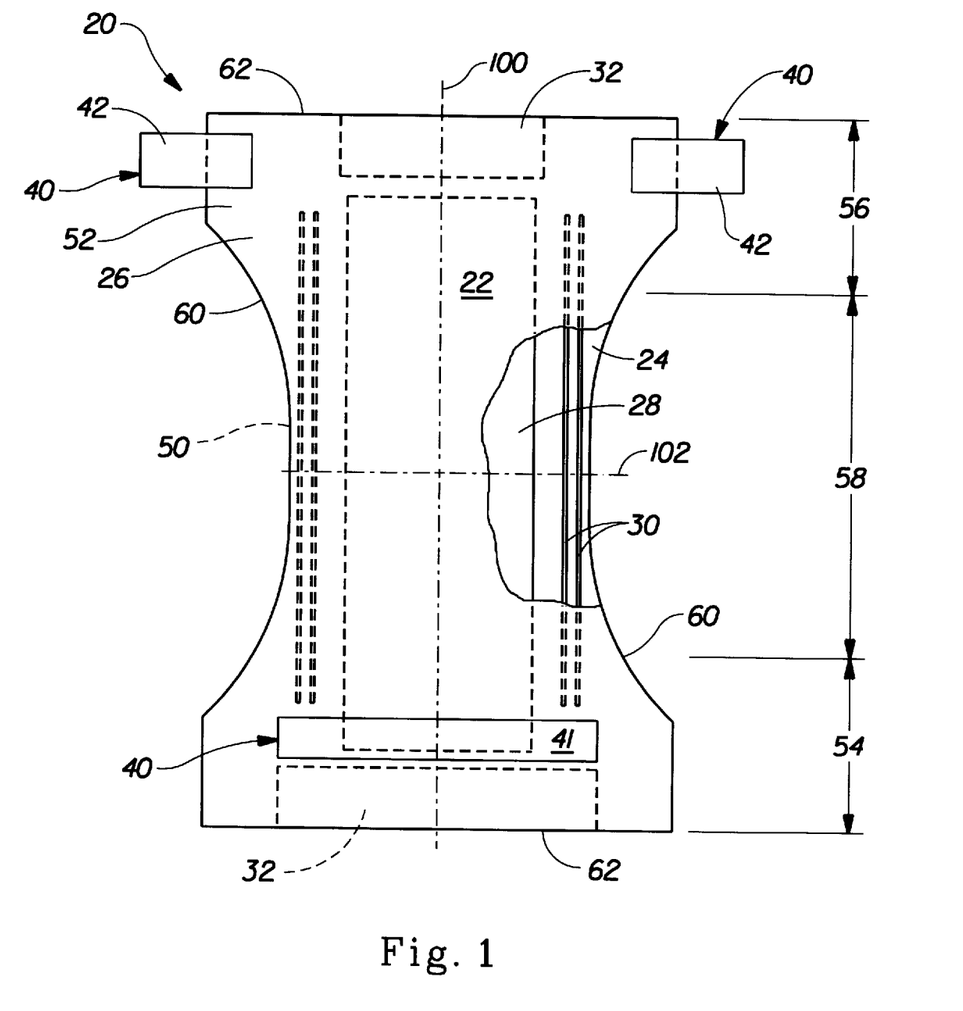
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined to the topsheet 24, and an absorbent core 28 positioned between the topsheet 24 and the backsheet 26. The diaper preferably further comprises elasticized leg cuffs 30; elasticized waistbands 32; a fastening system 40 comprising a pair of first fastening members 42 and a second fastening member 41.

The diaper 20 is shown in FIG. 1 to have an outer surface 52 (facing the viewer in FIG. 1), an inner surface 50 opposed to the outer surface 52, a front waist region 54, a rear waist region 56 longitudinally opposed to the front waist region 54, a crotch region 58 positioned between the front waist region 54 and the rear waist region 56, and a periphery which is defined by the outer perimeter or edges of the diaper 20 in which the longitudinal edges are designated 60 and the end edges are designated 62. The inner surface 50 of the diaper 20 comprises that portion of the diaper 20 which faces toward the wearer's body during use (i.e., the inner surface 50 is generally formed by at least a portion of the topsheet 24 and other components joined to the topsheet 24). The outer surface 52 of the diaper 20 comprises that portion of the diaper 20 which faces away from the wearer's body during use (i.e., the outer surface 52 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The front waist region 54 and the rear waist region 56 extend from the end edges 62 of the periphery to the crotch region 58.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction(which divides the wearer into front and back body halves.)

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge", which issued to Kenneth B. Buell et al on Sep. 29, 1992; each of which is incorporated herein by reference.

The diaper 20 also comprises a fastening system 40 having first fastening members 42 preferably comprising fastening tabs and a second fastening member 41 that can attach to one-another to form a side closure which maintains the front, waist region 54 and the rear waist region 56 in an overlapping configuration such that is lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; and the herein before referenced U.S. patent application Ser. No. 07/715,152; each of which is incorporated herein by reference.

Figure 2:
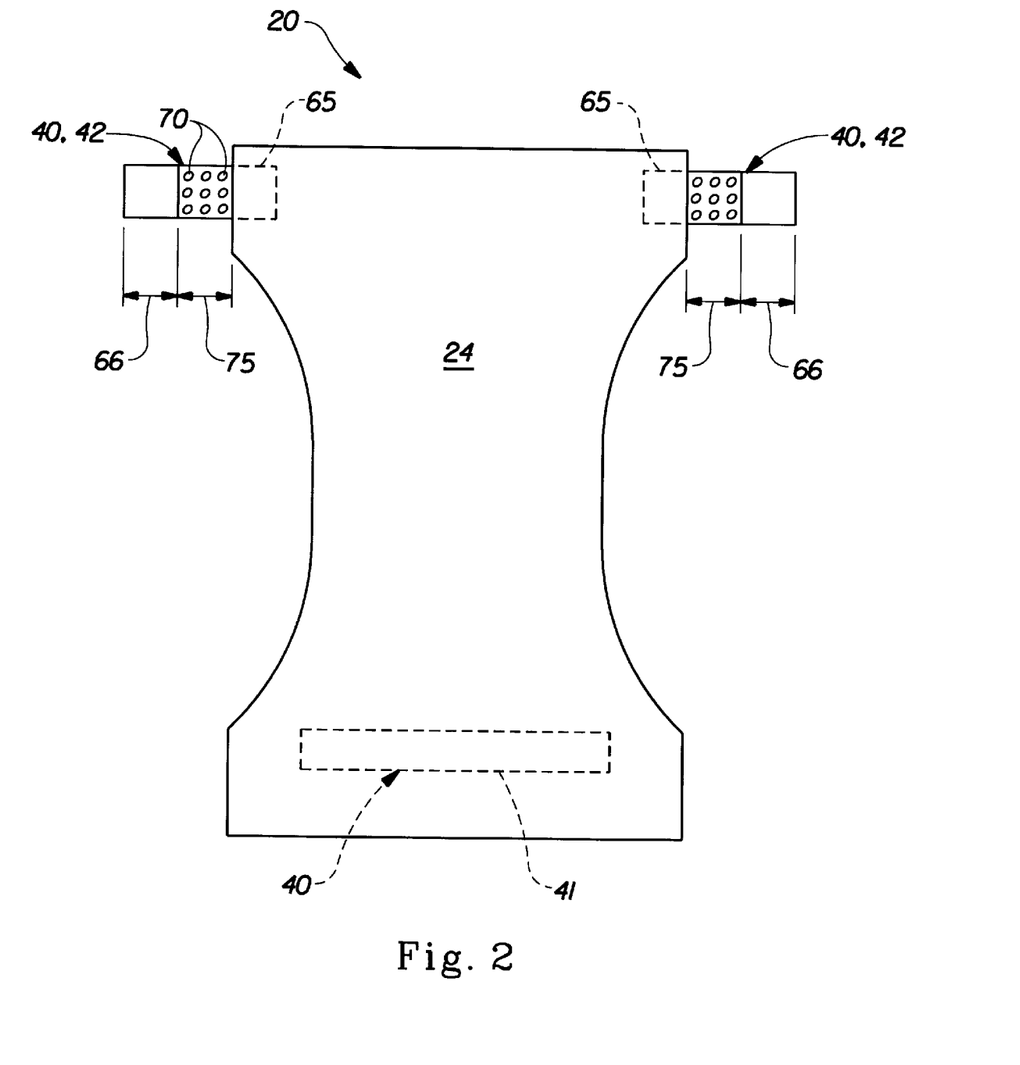
FIG. 2 is a plan view of another disposable diaper embodiment of the present invention disclosing a fastening system with adhesive tabs, the inner surface of the diaper facing the viewer.

FIG. 2 discloses a preferred embodiment of the fastening system 40 of the present invention. Disclosed herein are fastening tabs 42 having garment portions 65, end portions 66 and encapsulated portions 75 located between the garment portions 65 and the end portions 66. The encapsulated portions 75 comprise perfume-filled microcapsules 70 which are embedded within a preferable securement means such as an adhesive. An alternative embodiment is one as in FIG. 2 wherein the fastening tabs 42 contain no microcapsules 70; thus, the end portions 66 and secondary zones 75 contain adhesive only. The encapsulation zone 75 then becomes the secondary zone 75 when this zone contains no microcapsules 70. In such a construction, perfume-filled microcapsules are embedded on the second fastening member 41.

Figure 3:
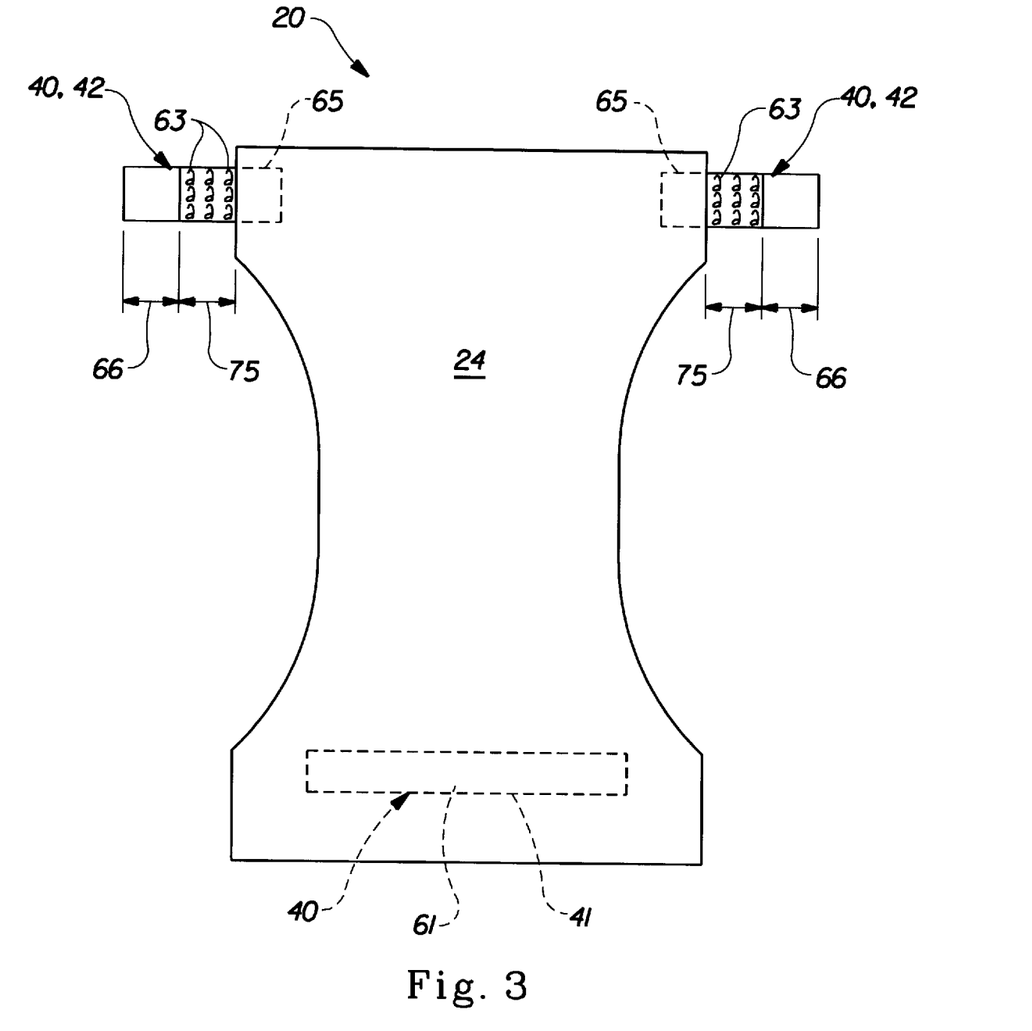
FIG. 3 is a plan view of another disposable diaper embodiment of the present invention disclosing a fastening system with combination adhesive and mechanical tabs, the inner surface of the diaper facing the viewer.

FIG. 3 discloses another embodiment of the fastening system 40. Disclosed herein are combination adhesive and hook fastening tabs 42 wherein the end portions 66 of the tabs 42 contain adhesive only. The encapsulated (or secondary) zone 75 comprises hooks 63 that will engage with the loops 61 of the second fastening member 41. Perfume-filled microcapsules 70 can be attached directly to the hooks 63. Also, the microcapsules 70 may be embedded within the secondary zone 75 by a securement means 90 (FIGS. 6A and 6B) at or near the attachment points of the hooks 63 to the tabs 42, i.e., secured to the surface of zone 75.

As discussed, one fastening system of the present invention comprises hook and loop type fasteners. As used herein, the term "hook and loop type fasteners" refers to fastening means comprising a "hook" component (hereinafter also referred to as an "engaging component") and a complementary loop component (hereinafter also referred to as a "landing component"). The term "hook" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary landing component.

Figure 4:
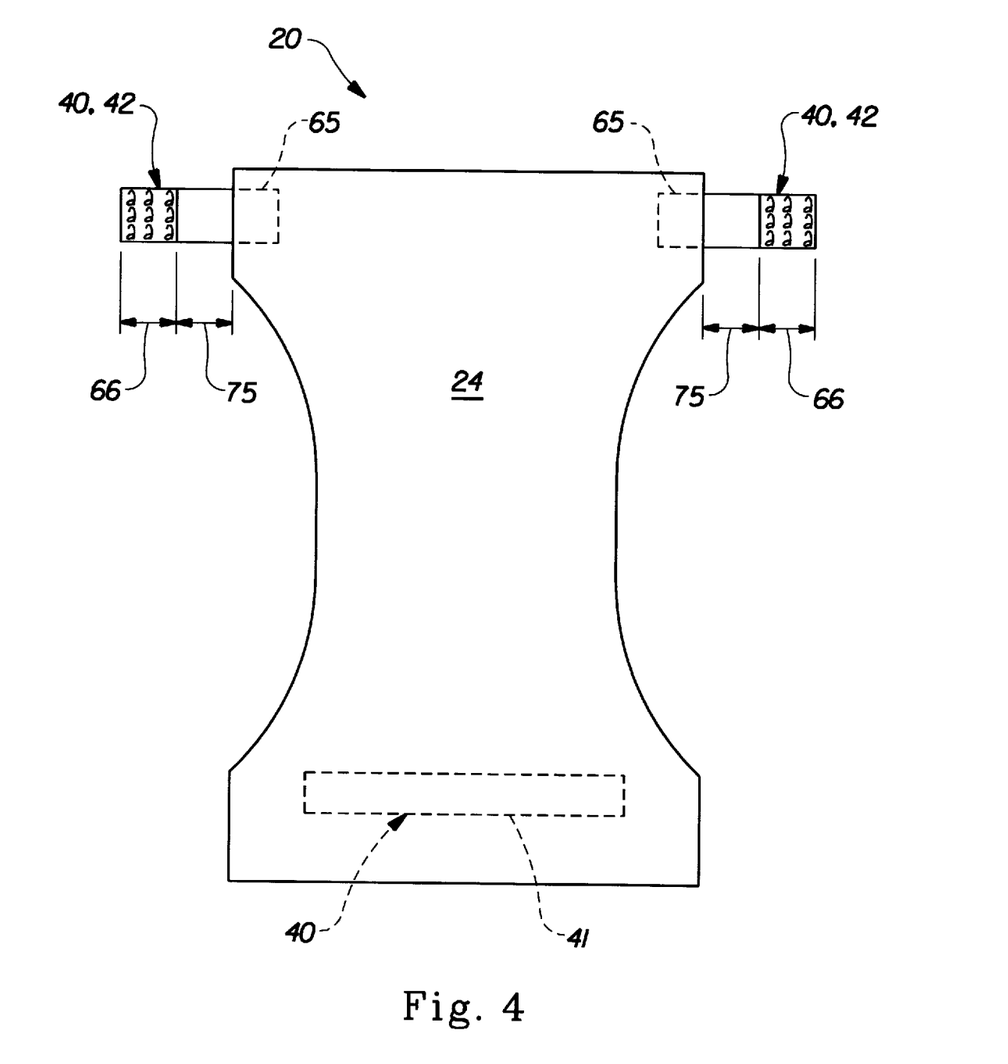
FIG. 4 is a plan view of another disposable diaper embodiment of the present invention disclosing a fastening system with combination adhesive and mechanical tabs, the inner surface of the diaper facing the viewer.

FIG. 4 discloses another embodiment of the fastening system 40 of the present invention. Disclosed herein are combination adhesive and hook fastening tabs 42 wherein the end portions 66 of the tabs 42 comprise hooks 63. Furthermore, microcapsules 70 are embedded at least partially on and/or within the end portions 66 preferably by a securement means 90 (FIGS. 6A and 6B), although any securement means known in the art to be compatible for use in a diaper 20 will suffice. The preferred embodiment in FIG. 4 contains perfume-filled microcapsules 70. Alternative embodiments are contemplated having tabs 42 which have no microcapsules 70 embedded within the end portions 66 and microcapsules 70 embedded only in the encapsulated zone 75 which would not comprise any hooks. Preferably, the encapsulated zone 75 would comprise an adhesive layer.

Figure 6A:
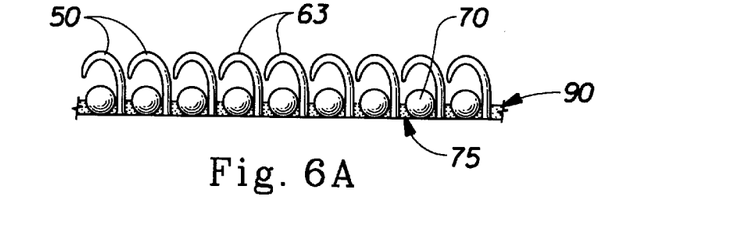
FIG. 6A is a side view of hook members attached to an encapsulation zone with microcapsules embedded within the securement means.
Figure 6B:
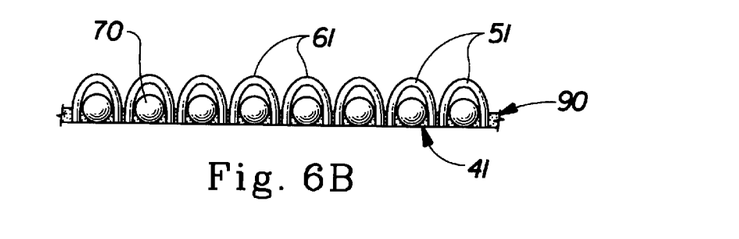
FIG. 6B is a side view of loop members attached to a second fastening member with microcapsules embedded within the securement means.

Specifically, in accordance with this invention, the securement means 90 of the fastening tabs 42, which surface is to contact the second fastening member 41, is provided with a multiplicity of small frangible microcapsules 70 containing perfume 95. FIGS. 6A and 6B illustrate such a securement means 90 containing perfume-filled microcapsules 70. Several methods may be used to adhere the microcapsules to the securement means 90 of the fastening tabs 42 and/or the second fastening, member 41. Preferably, a plurality of microcapsules dispersed in an adhesive may make up the securement means 90 of the fastening tabs 42 and/or second fastening member 41. A wide variety of adhesives will be suitable for this purpose, such as for example, polyethylene's, polyesters, polysiloxanes, acrylics, or block copolymers of styrene.

FIG. 6A discloses the side view of hooks 63 with microcapsules 70 embedded at least partially within a securement means 90. Preferable the microcapsules 70 are embedded within a securement means 90 comprising adhesive and are joined to the fastening member to form the encapsulation zone 75. Alternatively, microcapsules 70 can be joined directly to the hooks 63. FIG. 6B discloses the side view of loops 61 with microcapsules 70 embedded at least partially within a securement means 90 and preferably adhesively secured at points below the looping or connecting ends 51 of the loops 61. Preferably, microcapsules 70 are partially embedded within a securement means 90 such that a surface of the microcapsules 70 is left free to allow contact with a shearing means such as a tape tab, while the remaining portions of the microcapsules 70 are fixed to the surface of the encapsulation zone 75 to aid effective shearing of the microcapsules 70.

Preferably, at least 10% of the microcapsules 70 surface area will be secured and/or covered by a securement means 90 to aid effective shearing.

Figure 5:
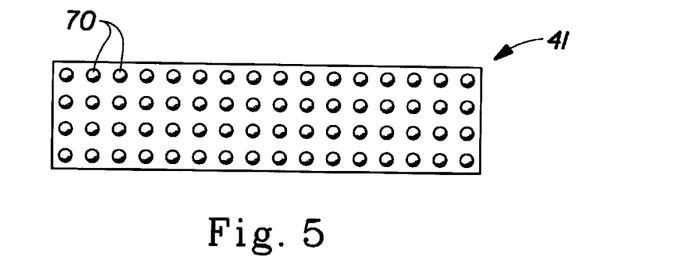
FIG. 5 is a plan view of a second fastening member with perfume-filled microcapsules embedded thereon.

FIG. 5 discloses a preferred second fastening member 41 that can be used with fastening tabs 42. With this second fastening member 41, fastening tabs 42 can either contain no microcapsules 70 or can contain microcapsules 70 in the encapsulated (or secondary) zone 75. As disclosed, microcapsules 70 can substantially cover the second fastening member 41 in a pre-determined configuration. However, the number of microcapsules present on the second fastening member 41 can range from one to any number desired by a manufacturer. Also, any configuration of the microcapsules 70 on the second fastening member 41 desired by a manufacturer can be provided.

Figure 5A:
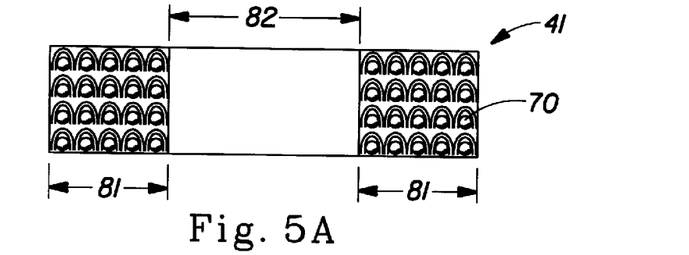
FIG. 5A is a plan view of a second fastening member divided for the use of mechanical and tape tab fasteners with perfume-filled microcapsules embedded thereon.

FIG. 5A discloses a second fastening member 41 portioned into loop zones 81 at the left and right ends of the second fastening member 41 and a fastening tab receiving zone 82 positioned centrally on the second fastening member 41. Microcapsules 70 are embedded or placed within the loop zone 81 preferably by an adhesive, but any securement means known in the art to be compatible for use in a diaper 20 will suffice. Another embodiment is a second fastening member 41 wherein microcapsules are embedded within the loop zone 81 and secured onto the tape receiving zone 82 by securement means preferably being adhesive. Also alternatively is a second fastening member 41 which contains microcapsules 70 embedded within the tape receiving zone 82 only.

Figure 5B:
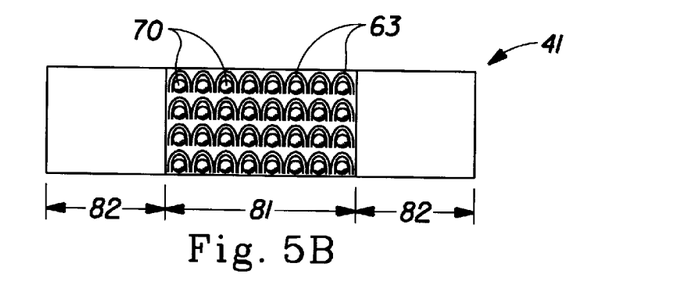
FIG. 5B is a plan view of a second fastening member divided for the use of mechanical and tape tab fasteners with perfume-filled microcapsules embedded thereon.

FIG. 5B discloses a preferred second fastening member 41 for the preferred combination tape and hook fastening tab 42 disclosed in FIG. 4. The loop zone 81 is placed centrally on the second fastening member 41 to receive the hooks 63 at the end portions 66 of the tabs 42 as shown in FIG. 4. In this embodiment microcapsules 70 are embedded within the loop zone 81 preferably by an adhesive securement means. In alternative embodiments of FIG. 5B, microcapsules 70 could be placed both in the tape receiving zones 82 and loop zone 81, thus providing microcapsules 70 substantially along the entire surface of the second fastening member 41. Again alternatively, microcapsules 70 may be placed in the tape receiving zone 82 only and not the hook zone 81. In an alternative embodiment to all of the second fastening members 41 disclosed, no microcapsules 70 would be embedded within the second fastening member 41, thus causing the tape and hook tabs 76 to contain all of the microcapsules 70 that are burst upon disengagement of the fastening system 40.

Figure 7:
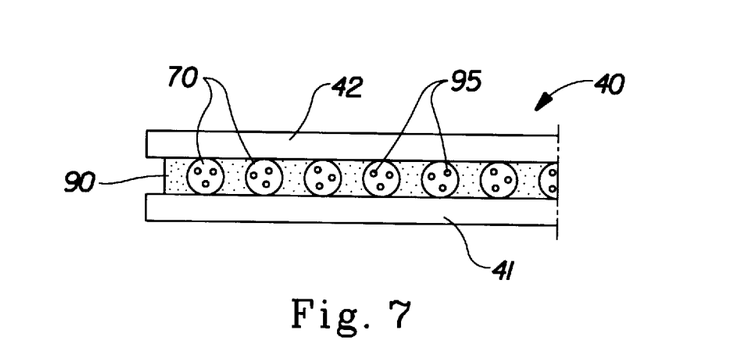
FIG. 7 is a side view of the microcapsules prior to disengagement of the first fastening member from the second fastening member.

FIG. 7 shows microcapsules 70 substantially embedded within adhesive securement means 90. The securement means 90 contacts the fastening tab 42 and the second fastening means 41. FIG. 7 demonstrates a side-by-side arrangement of two microcapsule types, but it would be obvious to any one skilled in the art that any physical arrangement of the microcapsules that produces the desired fragrance burst and/or diffusion perfume release may be utilized. Also, more than two types of microcapsules can be used to produced the desired fragrance characteristics; e.g., one type of microcapsule that produces a fragrance burst upon the shearing of microcapsules and a another type of microcapsule that diffuses perfume when the fastening system 40 is detached.

Figure 7A:
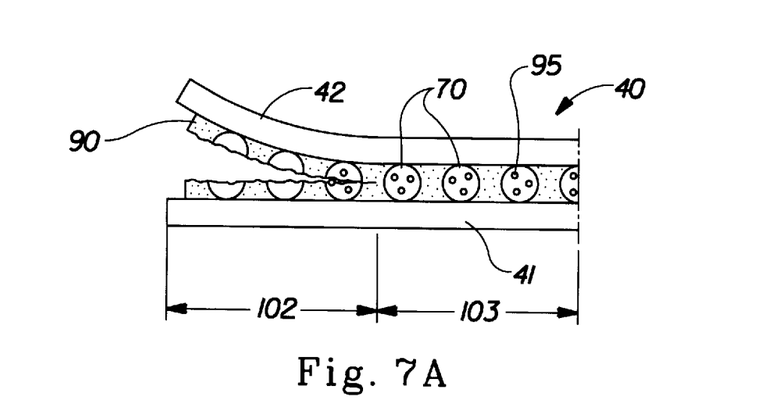
FIG. 7A is a side view of the microcapsules at disengagement of the first fastening member from the second fastening member.

FIG. 7A discloses a close-up side view of the interface of a fastening tape tab 42 and second fastening member 41 having microcapsules 70 therebetween during the act of disengagement of the fastening system 40. At disengagement a shear force is applied to the microcapsules 70 which causes a shearing or tearing away of at least the tops and/or unsecured portions of the microcapsules 70, thus releasing the perfume 95 therein.

FIG. 7A illustrates schematically one mechanism believed to be the operative one in insuring that a controlled amount of perfume 95 is released from the microcapsules 70 during use. Referring to the unpeeled portion 103 of the fastening tab 42, it can be seen that a portion of at least some of the microcapsules 70 are at least partially embedded within a layer of adhesive 90 when the fastening tab 42 is applied in its fastening position prior to use. Referring now to the peeled portion 102 of the fastening tab 42, it can be seen that the effects of peeling the fastening tab 42 produces a shear force across the tops of the microcapsules 70 and facilitates their rupture, thus releasing the perfume 95. Those factors which control the number of microcapsules 70 ruptured and hence the quantity of perfume 95 released can be entirely within the control of the manufacturer's discretion through manipulation of such parameters as microcapsule size and wall thickness, type of securement means used, quantity of securement means used, the amount and type of perfume used, rupture strength of the microcapsules, the number and distribution of the microcapsules, adhesive strength of an adhesive relative to the rupture strength of the microcapsules, and other such factors that may affect microcapsule rupture. In one example, it is believed that both the force required to pull a microcapsule from an adhesive or from the second fastening member should be greater than the force required to rupture a microcapsule. If this condition is met, microcapsules embedded within an adhesive rupture. In another example, microcapsules 70 sized at 50 microns or above should readily burst upon separation of the fastening tabs 42 from the second fastening member 41 because of increased effects upon adhesive and cohesive properties of materials in contact with the microcapsules 70.

Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference. When a two-point fastening system is used, the waist closure members of the waist closure system are preferably longitudinally aligned with the extensible front waist feature 42 and laterally aligned with the elastic strands of the extensible leg cuff 30 to provide an effective closure about both the legs and the waist. As shown throughout the disclosure, the diaper 20 may be provided with a pair of fastening tabs 42 that allow the side panels to be first joined together. The diaperer then brings the containment assembly 22 between the legs of the wearer and joins the assembly 22 to the outer layer of the waist feature. Such a configuration and securing method is more fully described in the above-referenced U.S. application Ser. No. 08/044,562(New, et al.)

The fastening system can comprise any attachment means known in the art including pressure sensitive adhesives, cohesive materials, mechanical fasteners such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

As discussed, one embodiment of the present invention comprises a hook fastening material preferably comprising a base and a plurality of engaging elements extending from the base. The hook fastening material is intended to engage fibrous elements of a loop fastening material so as to provide a secure fastening device. Thus, the hook fastening material may be manufactured from a wide range of materials. Further, the engaging elements may have any shape such as hooks, "T's", "mushrooms" or any other shape as are well known in the art Suitable materials include nylon, polyester, polypropylene, or any combination of these materials. Examples of preferred hook fastening materials are available from Aplix of Charlotte, N.C. under the trade designation 960, 957 and 942. Other preferred hook fastening materials are available from the Minnesota Mining and Manufacturing Company of St. Paul, Minn. under the trade designations CS200, CS300, MC5 and MC6. Another preferred hook fastening material is described in U.S. Pat. No. 5,058,247 entitled "Mechanical Fastening Prong" issued to Thomas Oct. 22, 1991 which is incorporated herein by reference.

The second fastening member preferably comprises a fastening element engageable with the hook member. Thus, the second fastening member may be manufactured from a wide range of materials and configurations capable of securely engaging the hook member. For example, the second fastening member may comprise identical complementary elements or distinct complementary elements. As used herein, the term "identical complementary elements" is used to define mechanical fastening systems wherein the engaging elements of the hook member and the second fastening member comprise the same configuration or structure that are interlocking. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the hook member is different from the second fastening member but is engageable therewith.

In one preferred embodiment, the second fastening component comprises a plurality of fiber elements, such as a loop fastening material, that engage the engaging elements of the hook component. The loop fastening material may be manufactured from a wide range of materials to provide fiber elements, preferably being loops. Suitable materials include woven materials, nonwovens, nylons, polyesters, polypropylenes, or any combination of these materials. One suitable loop fastening material is a nonwoven available from Minnesota Mining and Manufacturing Company, St. Paul, Minn. under the trade designation EBL. A preferred loop fastening material comprises a number of shaped engaging elements projecting from a woven backing such as the commercially available material designated Guilford 18904 available from Guilford Mills of Greensboro, N.C. Other suitable loop components are available from the Minnesota Mining and Manufacturing Company of St. Paul, Minn. under the trade designation EBL. An inexpensive loop fastening material and a method of making the same is described in U.S. Pat. No. 5,032,122, entitled "Loop Fastening Material For Fastening Device and Method of Making Same" issued to Noel et al., Jul. 16, 1991, which application is incorporated herein by reference. Another suitable loop material is described in U.S. Pat. No. 5,326,612 entitled "Nonwoven Female Component for Refastenable Fastening Device and Method of Making the Same" issued to David J. K. Goulait on Jul. 5, 1994, which is hereby incorporated by reference herein. Yet other suitable second fastening components are described in co-pending U.S. patent application Ser. No. 08/254,814 entitled "Nonwoven Female Component For Refastenable Fastening Device and Method of Making the Same" filed Jun. 6, 1994 in the names of Patrick Jay Allen et al.; U.S. patent Ser. No. 08/287,571 entitled "Nonwoven Female Component For Refastenable Fastening Device" filed Aug. 9, 1994 in the names of Willie F. King et al.; and U.S. patent Ser. No. 08/374,269 entitled, "Female Component For Refastenable Fastening Device" filed Jan. 18, 1995 in the names of Carl L. Bergman et al.

The fastening elements may be disposed on either the outer surface or the inner surface of the diaper 20. In a preferred embodiment, however, the fastening elements are disposed on the diaper 20 such that the fasteners do not irritate the wearer's skin. In addition, the fastening elements may either be a discrete separate element affixed to the diaper 20 or a unitary piece of material that is neither divided nor discontinuous with an element of the diaper 20 such as the topsheet 24 or the backsheet 26. While the fastening elements can assume varying sizes and shapes, they preferably comprise one or more separate patches of material joined to the diaper 20 to allow for the best fit for a broad range of wearers.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids which have passed through the topsheet and are contained in the absorbent core 28 (i.e., to prevent rewet). If the topsheet is made of a hydrophobic material, at least the upper surface thereof is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the material with the surfactant and immersing the material in the surfactant. A more detailed discussion of such a treatment and hydrophilicity is contained in U.S. Pat. No. 4,988,344 entitled "Absorbent Articles With Multiple Layer Absorbent Layers" issued to Reising, et al. on Jan. 29, 1991.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern touch as is illustrated by the apparatus and methods shown in U.S. Pat. No. 3,911,173 issued to Sprague, Jr. on Oct. 7, 1975; U.S. Pat. No. 4,785,996 issued to Ziecker, et al. or Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, heat/pressure bonds ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). The backsheet preferably comprises a polyethylene blend film of about 0.025 mm (1.0 mil) as is manufactured by Tredegar Corporation of Terre Haute, Ind. and marketed as P8863.

The absorbent core 28 may be any absorbent means which is capable of absorbing and retaining liquids such as urine and other certain body exudates. The absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. FIG. 1 shows a preferred embodiment of the diaper 20 having a rectangular-shape absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 5,147,345 entitled "High Efficiency Absorbent Articles For Incontinence Management", issued to Young, LaVon & Taylor on Sep. 15, 1992; U.S. Pat. No. 5,102,597 entitled "Porous, Absorbent, Polymeric Macrostructures and Methods Of Making the Same", issued to Roe, Lahrman and Berg on Apr. 7, 1992; and U.S. Pat. No. 4,834,735, entitled "High Density Absorbent Members Having Lower Density and Lower Basis Weight Acquisition Zones", issued to Alemany and Berg on May 30, 1989; also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these patents are incorporated herein by reference.

In a preferred embodiment of the present invention, an acquisition layer(s) may be positioned between the topsheet 24 and the absorbent core 28 and joined to the absorbent core 28. The acquisition layer may serve several functions including improving wicking of exudates over and into the absorbent core. There are several reasons why the improved wicking of exudates is important, including providing a more even distribution of the exudates throughout the absorbent core 28 and allowing the absorbent structure to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent structures disclosed herein having an acquisition layer and a topsheet are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet 24 and separate from the inserted absorber material or absorbent core 28 by any of the conventional means for joining webs together, most preferably by fusion bonds as is more fully described in the above-referenced Cree application.

The diaper 20 preferably further comprises extensible leg cuffs 30 for providing improved containment of liquids and other body exudates. Each extensible leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbents article having leg cuffs having a relatively low ultimate contact force at relatively high elongation's accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference.

The diaper 20 further comprises extensible waist features that provide improved fit and containment. The extensible waist features at least extend longitudinally outwardly from the containment assembly 22, preferably a respective waist edge of the absorbent core 28, and generally form at least a portion of the end edge of the diaper 20. While a disposable diaper of the present invention is constructed with an extensible waist feature disposed in each waist region (an elastic waist feature 32 and an extensible front waist feature 42), the discussion will focus on diapers having different configurations for each extensible waist feature. At a minimum, it is preferred that the diaper at least have one of the extensible waist features constructed according to the present invention, more preferably at least the elastic waist feature 32. The waist features can be constructed as a separate element joined to the containment assembly 22 or as an extension of other elements of the diaper (i.e., unitary). The waist features will be described with respect to preferred embodiments in which certain portions or panels comprise an extension of other elements of the diaper such as the backsheet 26, the topsheet 24, or both, and other portions or panels comprise a separate element joined to other portions or panels of the waist feature or other panels of the diaper.

As used herein, the term "cyclodextrin" includes any of the known cyclodextrins such as unsubstituted cyclodextrins containing from six to twelve glucose units, especially, alpha-, beta-, and gamma-cyclodextrins, and/or their derivatives, and/or mixtures thereof. The alpha-cyclodextrin consists of 6, the beta-cyclodextrin 7, and the gamma-cyclodextrin 8, glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. Nos.: 3,426,011, Parmerter et al., issued Feb. 4, 1969; 3,453,257, 3,453,258, 3,453,259, and 3,453,260, all in the names of Parmerter et al., and all also issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use herein are methyl-beta-cyclodextrin, hydroxyethyl-beta-cyclodextrin, and hydroxypropyl-beta-cyclodextrin of different degrees of substitution (D.S.), available from Amaizo; Wacker Chemical (USA), Inc.; and Aldrich Chemical Company. Water-soluble derivatives are also highly desirable.

The compositions and articles of this invention optionally contain, in addition to uncomplexed, small particle size cyclodextrins, an effective, i.e., odor-controlling, amount of various additional adjunct odor-controlling materials. Incorporating adjunct odor-controlling materials will enhance cyclodextrin's capacity for controlling odors, as well as the range of odor types being controlled. Such materials include, for example, zeolites, activated carbon, kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like. Especially preferred is zeolite material having "intermediate" silicate/aluminate ratios.

A wide variety of intermediate zeolites suitable for use herein are commercially available as VALFOR CP301-68, VALFOR 300-63, VALFOR CP300-35 and VALFOR CP300-56, from PQ Corporation, and the CBV100 series (other than Mordenite, as noted below) of zeolites from Conteka.

In the event the zeolites herein are optionally to be used in conjunction with the activated carbon, it is preferred (for visually aesthetic purposes) to coat the carbon with the zeolite using a binder.

Other odor-controlling agents include kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like.

The encapsulated agents ingredients and compositions of this invention, are the conventional ones known in the art. Selection of any encapsulated agents component, or amount of encapsulated agents, is based on functional and aesthetic considerations. Preferred encapsulated agents components useful in the present invention are the highly volatile, and the moderately volatile encapsulated agents ingredients, more preferably the highly volatile, low boiling ingredients.

The highly volatile, low boiling, encapsulated agents ingredients typically have boiling points of about 250° C. or lower. These highly volatile encapsulated agents ingredients are fleeting and are quickly lost as they are released. Many of the more moderately volatile encapsulated agents ingredients are also quickly lost. The moderately volatile encapsulated agents ingredients are those having boiling points of from about 250° C. to about 300° C. Many of the encapsulated agents ingredients as discussed hereinafter, along with their odor characters, and their physical and chemical properties, such as boiling point and molecular weight, are given in "Encapsulated agents and Flavor Chemicals (Aroma Chemicals)," Steffen Arctander, published by the author, 1969, incorporated herein by reference.

Examples of the highly volatile, low boiling, encapsulated agents ingredients are: anethole, benzaldehyde, benzyl acetate, benzyl alcohol, benzyl formate, isobornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevomenthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile encapsulated agents ingredients. For example, lavandin contains as major components: linalool; linalyl acetate; geraniol; and citronellol. Lemon oil and orange terpenes both contain about 95% of d-limonene.

Examples of moderately volatile encapsulated agents ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood trepenes are composed mainly of alpha-cedrene, beta-cedrene, and other $C_{15}H_{24}$ sesquiterpenes.

The encapsulated agents/cyclodextrin inclusion complexes of this invention are formed in any of the ways known in the art. Typically, the complexes are formed either by bringing the encapsulated agents and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it results in smaller particles so that there is less, or no, need to reduce the particle size. In addition, less solvent is needed and therefore less separation of the solvent is required. Disclosures of complex formation can be found in Atwood, J. L., J. E. D. Davies & D. D. MacNichol, (Ed.): *Inclusion Compounds, Vol. III*, Academic Press (1984), especially Chapter 11, Atwood, J. L. and J. E. D. Davies (Ed.): *Proceedings of the Second International Symposium of Cyclodextrins* Tokyo, Japan, (July, 1984), and J. Szejtli, *Cyclodextrin Technology* Kluwer Academic Publishers (1988), said publications incorporated herein by reference.

Microcapsules 70 for use in this invention can be made by many of several well-known encapsulating processes. Examples of appropriate processes include chemical encapsulating processes and mechanical encapsulating processes. A wide variety of processes exist by which microcapsules 70 can be manufactured. These varied processes provide different techniques for producing microcapsules 70 of varying sizes, alternative materials for the composition of the capsule shell and various different functional materials within the shell. Some of these various processes are shown in U.S. Pat. Nos. 3,516,846; 3,516,941; 3,996,156; 4,409,156 and 5,180,637 and British patent specification Nos. 1,156,725; 2,041,319 and 2,048,206, and each is incorporated herein by reference.

It is also desirable to have microcapsule construction resist the effects of variable ambient conditions. It is therefore desirable that rupture strength exceed 4.0 g/cm after storage at 120° C., and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 2 and 90 g/cm at 20° and 50% R.H. The use of microcapsules 70 which are not moisture sensitive in combination with these large microcapsules 70 (i.e., greater than 30 microns and up to 50 microns) provides a useful microcapsule-containing adhesive layer 90.

An example of a mechanical encapsulating process is the impingement of droplets of the material to be encapsulated (i.e., in the case of this invention, a encapsulated agents or other deodorant composition) upon liquid or semi-solid films of intended capsule wall material; separation of the thereby encapsulated droplet from the film of impingement; and solidification of the microcapsule wall material.

Chemical encapsulating processes generally include combining a first reactive material in a continuous phase capsule manufacturing vehicle and a second reactive material into droplets to be encapsulated. The droplets are then dispersed in the manufacturing vehicle and a reaction between the reactive materials is effected, Liquid-liquid phase separation of the polymeric capsule wall material from the vehicle is carried out wherein the phase-separated polymeric material wets and enwraps the dispersed droplets to be encapsulated.

A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and British patent specification Nos. 2,006,709 and 2,062,570, and each is incorporated herein by reference.

Adhesive securement means 90 will preferably form a bond to the coated surfaces of the fastening tabs 42 and second fastening member 41 which is stronger than the cohesive strength of the adhesive with the microcapsules dispersed therein. While not wishing to be bound by any particular theory, it is believed that this would allow effective shearing of the microcapsules 70 at disengagement of the fastening system 40. Although it is generally desirable to have an adhesive, the absolute cohesive strength of which is less than its adhesive strength to the surface of the fastening tabs 42 and second fastening member 41, this is not essential. When microcapsules 70 are included within the adhesive composition 90, the effective cohesive strength of the adhesive tends to be reduced. Adhesives, which by themselves would cause the tabs 42 and second fastening member 41 to be damaged during separation, can be used in combination with microcapsules 70 in the practice of the present invention because of lowered effective cohesive strength.

An adhesive securement means 90 bearing microcapsules 70 can be coated onto a portion of the adhering surface of the fastening tabs 42 and/or at least a portion of the second fastening strip 41. This adhesive may be the sole bonding material between the fastening tabs 42 and second fastening member 41 and the sheets. Alternatively, two adhesives may be used in which one holds the microcapsules 70 to a portion of the fastening tab 42 and the other adhesive is used to secure the tab end portions 66 to the second fastening member 41. If any effective amount of adhesive is present in the areas where microcapsules 70 are deposited with the intention of having them removable and not rupture due to separation of the fastening tabs 42 from the second fastening member 41, it is then preferable that the cohesive strength of that adhesive be lower than the rupture strength of the microcapsules 70.

It has also been found that microcapsule size plays a role in the usefulness of microcapsules 70 according to the practice of the present invention. Generally the microcapsules 70 should have an average diameter between 5 and 100 microns and preferably between 12 and 30 microns when the capsule payload is between 80 and 90% by weight of the total capsule weight. It is highly preferred that the microcapsules 70 have an average diameter between 14 and 42 microns and it is most preferred that the microcapsules 70 have a diameter between 15 and 25 microns. These dimensions play a surprisingly important role in the ability to control the percentage of rupture of microcapsules 70 in the practice of the present invention. With lower payloads (e.g., 70–80%), the microcapsules 70 should be larger to provide the necessary rupture strength. The broadest range of average capsule size under most conditions would be about 5 to 100 microns. When 8 micron microcapsules 70 are used, a 90–95% by weight payload is preferred. Generally preferred are microcapsules 70 having sizes of between 8 and 30 micrometers.

The microcapsules 70 can form between 20 and 99 percent by volume of the total adhesive composition of the fastening tabs 42, but most preferably between 30 and 75 percent of this total composition volume. The absolute peel force tends to be dependent on the weight of the base coat and relatively independent of the amount of microcapsules 70 (up to 50% by weight of microcapsules 70 per unit area).

It is preferred that the microcapsules 70 have an average diameter between 5 and 100 micrometers, the cohesive strength of the adhesive composition layer being less than the strength of the bond between said adhesive composition and a coated face of the fastening tab 42 and the second fastening member 41, the tensile rupture strength of the microcapsules 70 being less than the cohesive strength of the adhesive composition, and the rupture force of the microcapsule containing adhesive composition layer at 50% relative humidity being between at least 0.5 ounces per linear five-and-one half inches (greater than 1.0 g/cm and less than 20 g/cm). It is preferred that the rupture strength of the microcapsules 70 exerted by the fastening tabs 42 and second fastening member 41 exceeds 2.0 g/cm and is less than 16 g/cm and most preferably exceeds 2.5 g/cm and is less than 10 g/cm.

In most preferable embodiments, the nature and composition of the adhesive is not critical to the practice of the invention as long as the adhesive is capable of adherently bonding the microcapsules 70 to the substrate. The quantity of adhesive must be sufficient to hold the microcapsules 70 in place on the surface of the substrate until rupture of the microcapsules 70 at removal of the diaper 20 from the wearer. Any class of adhesives including but not limited to polyurethane's, polyacrylates, polyvinyl resins (e.g., polyvinyl alcohol, polyvinyl chloride), polyamides, polyesters, polyolefins, starches, gum arabic, gelatin and the like may be readily used in the practice of the present invention.

Preferably, the adhesive used as the securement means 90 is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Washing of the microcapsules 70 before mixing them with the adhesive often tends to provide more consistency in their properties by removing low molecular weight, unreacted materials.

In another aspect, the present invention involves a novel article comprising a thermoplastic, preferably flexible, substrate having partially embedded therein rupturable microcapsules 70. In this embodiment, binder resin is required. This article can be used in situations where good retention and protection of microcapsules is required, but where access to the microcapsules 70 must be retained. Methods for applying the binder (with microcapsules) to the substrate can vary, depending upon available methods and economics more than any other parameter. Suitable application methods include air knife, gravure coating, and printing methods including silk screening, gravure, and flexographic techniques. The binder (with microcapsules) may be applied either in a continuous or discontinuous pattern on the substrate.

Capsule wall materials suitable for use in accordance with the teachings of this invention include any appropriate polymeric film-forming material. For example, microcapsules 70 may be made from natural hydrophilic polymeric materials such as gelatin, gum arabic, starch, carrageenin, and zein; natural polymeric materials modified in some way such as ethyl cellulose, carboxymethyl cellulose, shellac, resin and nitrocellulose; and other polymeric materials such as polyvinyl alcohol, polyethylene, polystyrene, polyacrylamide, polyether, polyester, polybutadiene, silicone, epoxy and polyurethane.

The particular encapsulated agents 95 or deodorant encapsulated forms no part of this invention and may be varied to so great a degree as to defy classification or description. Reference is made, instead, to "Cosmetics, Science and Technology," second edition, edited by M. S. Balsam and Edward Sagarin and published by John Wiley & Sons, Inc., of New York, 1972. In particular, reference is made to Chapter 32, "Fragrance" written by M. S. Balsam for examples of the variety of encapsulated agents formulations possible.

The material contained in the microcapsules 70 can be any of a variety of liquids, including solutions, dispersions, and gelled materials. Preferred types of ingredients are organic solids which are fragrance-releasing materials that readily volatilize upon rupturing of the microcapsules 70. The most preferred types of ingredients would be fragrant materials (such as essences and most preferably medium to highly volatile perfumes) or materials which provide chemically active vapors or liquids (e.g., bacteriostats or deodorants). Whatever the fragrance, it or they should be chosen to be compatible with the fastening system 40 and all other diaper components.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper to be fitted about the lower torso of a wearer having a first waist region and a second waist region, comprising:

a fluid pervious topsheet;

a fluid impervious backsheet joined to said topsheet;

an absorbent core located between said topsheet and said backsheet;

a fastening system for securing said diaper on a wearer; said fastening system comprising at least one pair of first fastening members disposed in said first waist region and at least one second fastening member disposed in said second waist region, said first fastening members and said second fastening member being attached and positioned in an overlapping configuration such that lateral tensions are maintained about the torso of wearer to maintain said diaper about the wearer; and a plurality of perfume-filled release agents disposed on said fastening system, said perfume-filled release agents being released upon disengagement of said fastening system.

2. The diaper of claim 1 wherein said perfume-filled release agents are microcapsules.

3. The diaper of claim 2 wherein said perfume-filled release agents are selected from the group consisting of uncomplexed cyclodextrins, perfumes, zeolites, is activated carbons and mixtures thereof.

4. The diaper of claim 2, wherein said first fastening member comprises hooks.

5. The diaper of claim 4, wherein said second fastening member comprises loops.

6. The diaper of claim 2, wherein said first fastening member comprises adhesive tape tabs.

7. The diaper of claim 2, wherein said second fastening member comprises a tape tab receiving zone.

8. The diaper of claim 2, wherein said first fastening member comprises said adhesive tape tabs and said hooks.

9. The diaper of claim 8, wherein said second fastening member comprises said loops and a at least one said tape tab receiving zone.

10. The diaper of claim 2, wherein said microcapsules are joined to said first fastening member of said fastening system.

11. The diaper of claim 2, wherein said microcapsules are joined to said second fastening member of said fastening system.

12. The diaper of claim 2, wherein said microcapsules are joined to said first fastening members and said second fastening member of said fastening system.

13. The diaper of claim 2 wherein said microcapsules provide a fragrance burst at disengagement of said first and second fastening members.

14. The diaper of claim 13 wherein said microcapsules diffusely release perfume at a steady-state at disengagement of said first and second fastening members.

15. The diaper of claim 2 wherein said microcapsules provide a fragrance burst at engagement of said first and second fastening members.

16. The diaper of claim 15 wherein said microcapsules diffusely release perfume at a steady-state at disengagement of said first and second fastening members.

* * * * *